US00PP35259P2

(12) United States Plant Patent
Roberts et al.

(10) Patent No.: US PP35,259 P2
(45) Date of Patent: Jul. 11, 2023

(54) ***VITEX* PLANT NAMED 'BAILTEXTHREE'**

(50) Latin Name: *Vitex agnus-castus*
Varietal Denomination: Bailtexthree

(71) Applicant: Bailey Nurseries Inc., Newport, MN (US)

(72) Inventors: David Jonathan Roberts, Athens, GA (US); Justin Schulze, Athens, GA (US); Oren McBee, Bishop, GA (US)

(73) Assignee: BAILEY NURSERIES INC., Newport, MN (US)

( * ) Notice: Subject to any disclaimer, the term of this patent is extended or adjusted under 35 U.S.C. 154(b) by 0 days.

(21) Appl. No.: 17/942,998

(22) Filed: Sep. 12, 2022

(51) Int. Cl.
*A01H 6/00* (2018.01)
*A01H 5/02* (2018.01)

(52) U.S. Cl.
USPC ..... Plt./226

(58) Field of Classification Search
USPC ..... Plt./226
CPC ..... A01H 6/00; A01H 5/02
See application file for complete search history.

*Primary Examiner* — Keith O. Robinson
(74) *Attorney, Agent, or Firm* — Penny J Aguirre

(57) ABSTRACT

A new cultivar of *Vitex* plant named 'Bailtexthree' that is characterized by its a medium plant size, its early flowering period, its re-blooming habit without deadheading, and its resistance to leaf spot.

4 Drawing Sheets

Botanical classification: *Vitex agnus-castus*.
Variety denomination: 'Bailtexthree'.

BACKGROUND OF THE INVENTION

The present invention relates to a new and distinct cultivar of *Vitex agnus-castus*. The new *Vitex* will hereafter be referred to by its cultivar name, 'Bailtexthree'. 'Bailtexthree' is a new cultivar of *Vitex agnus-castus* grown for use as an ornamental landscape plant.

The new cultivar was derived from a controlled breeding program in summer of 2015 conducted by the Inventors in Watkinsville, Ga. 'Bailtexthree' arose from open pollination of *Vitex agnus-castus* 'PIIVAC-II' (U.S. Plant Pat. No. 26,775) as the female parent. The male parent is therefore unknown. 'Bailtexthree' was selected as a single unique plant from the progeny of the open-pollination in summer of 2016 after evaluation for growth habit, foliage, and flower characteristics.

Asexual propagation of the new cultivar was first accomplished by softwood stem cuttings by one of the Inventors in Watkinsville, Ga. in summer of 2018. Asexual propagation by softwood stem cuttings has determined that the characteristics of the new cultivar are stable and are reproduced true to type in successive generations.

SUMMARY OF THE INVENTION

The following traits have been repeatedly observed and represent the characteristics of the new cultivar. The attributes in combination distinguish 'Bailtexthree' as a unique cultivar of *Vitex*.

1. 'Bailtexthree' exhibits a medium plant size.
2. 'Bailtexthree' exhibits an early flowering period.
3. 'Bailtexthree' exhibits re-blooming habit without deadheading.
4. 'Bailtexthree' exhibits resistance to leaf spot.

The female parent plant differs from 'Bailtexthree' in having a more compact plant habit, a later flowering period, and in being susceptible to leaf spot. 'Bailtexthree' can be most closely compared to *Vitex* 'Shoal Creek' (not patented) and 'PIIVAC-1' (U.S. Plant Pat. No. 25,914). 'Shoal Creek' is similar to 'Bailtexthree' in having purple color flowers. 'Shoal Creek' differs from 'Bailtexthree' in having a larger size plant habit, a later flowering period, and in being more susceptible to leaf spot. 'PIIVAC-1' is similar to 'Bailtexthree' in having a rounded, shrubby plant habit and a similar plant size. 'PIIVAC-1' differs from 'Bailtexthree' in having a later flowering period, more susceptibility to leaf spot, less of a reblooming habit and flowers that are blue-purple in color.

BRIEF DESCRIPTION OF THE DRAWINGS

The accompanying color photographs illustrate the overall appearance and distinct characteristics of the new *Vitex*.

The photograph in FIG. 1 was taken of a plant 6 years in age as grown in a trial garden in Watkinsville, Ga. and provides a view of the plant habit of 'Bailtexthree' in bloom.

The photographs in FIG. 2 through FIG. 5 were taken of a 1-year-old plant as grown in a 2-gallon container in Cottage Grove, Minn.

Figure 1:
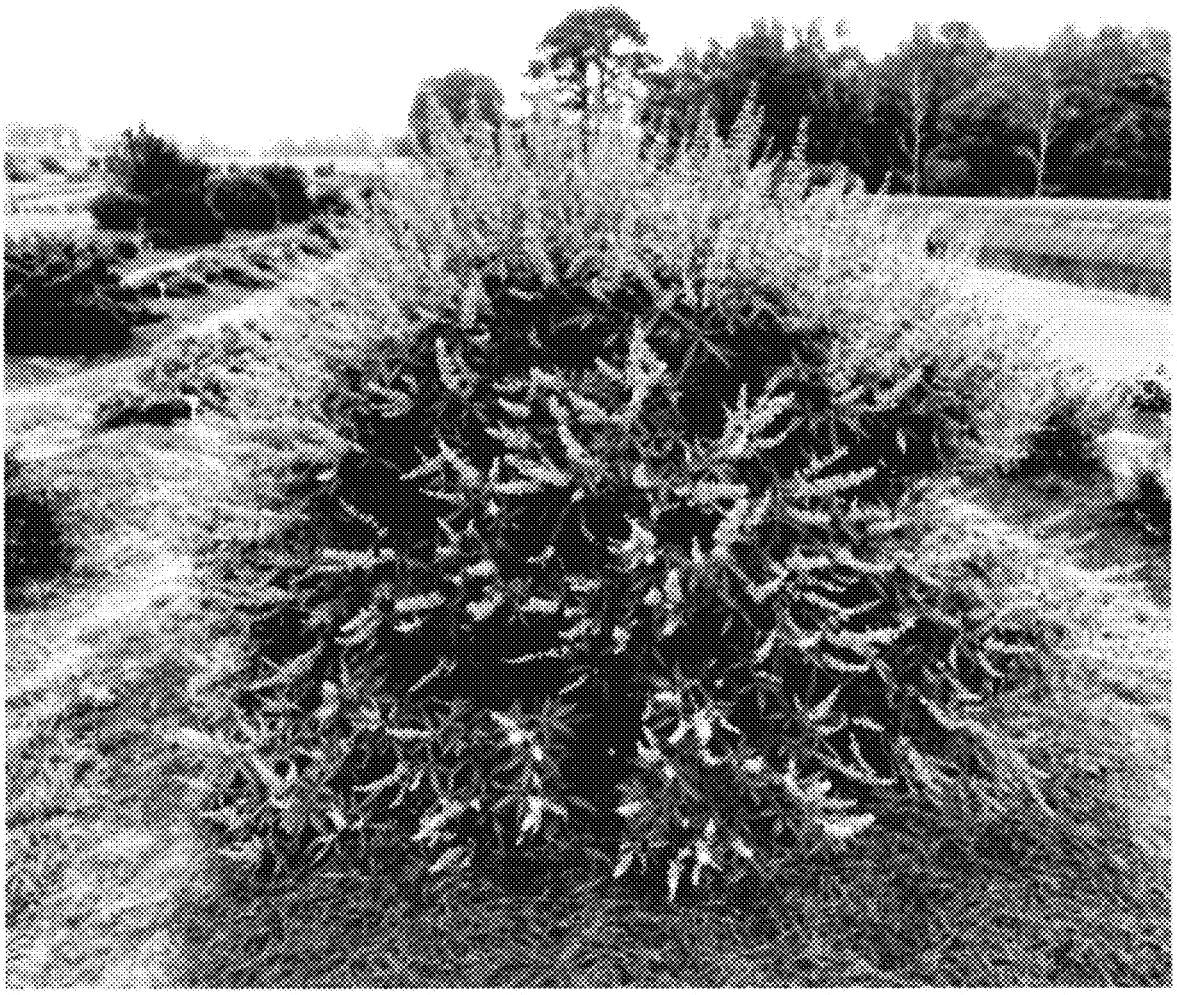
Figure 2:
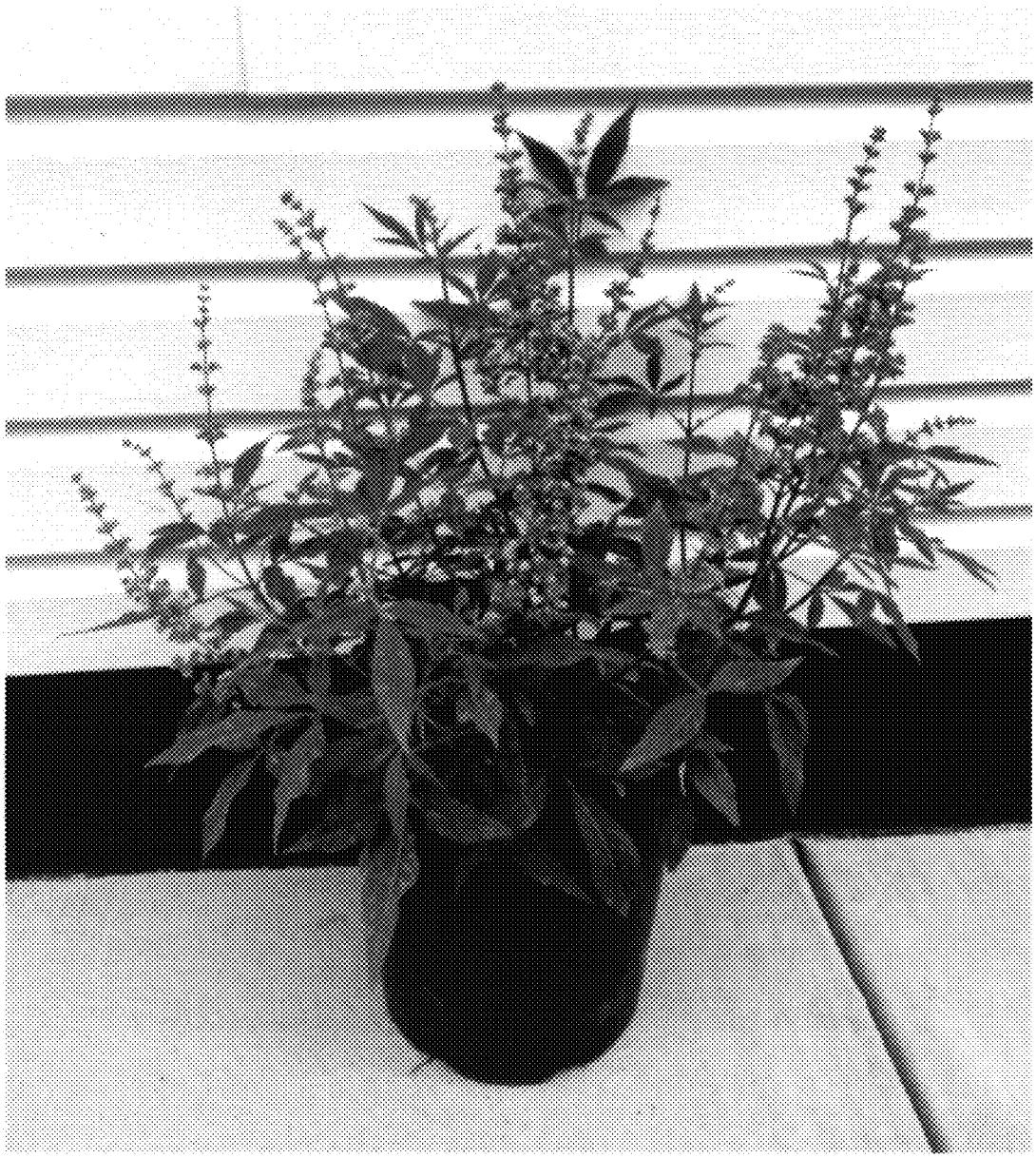

The photograph in FIG. 2 provides a side view of a plant of 'Bailtexthree' in bloom.

Figure 3:
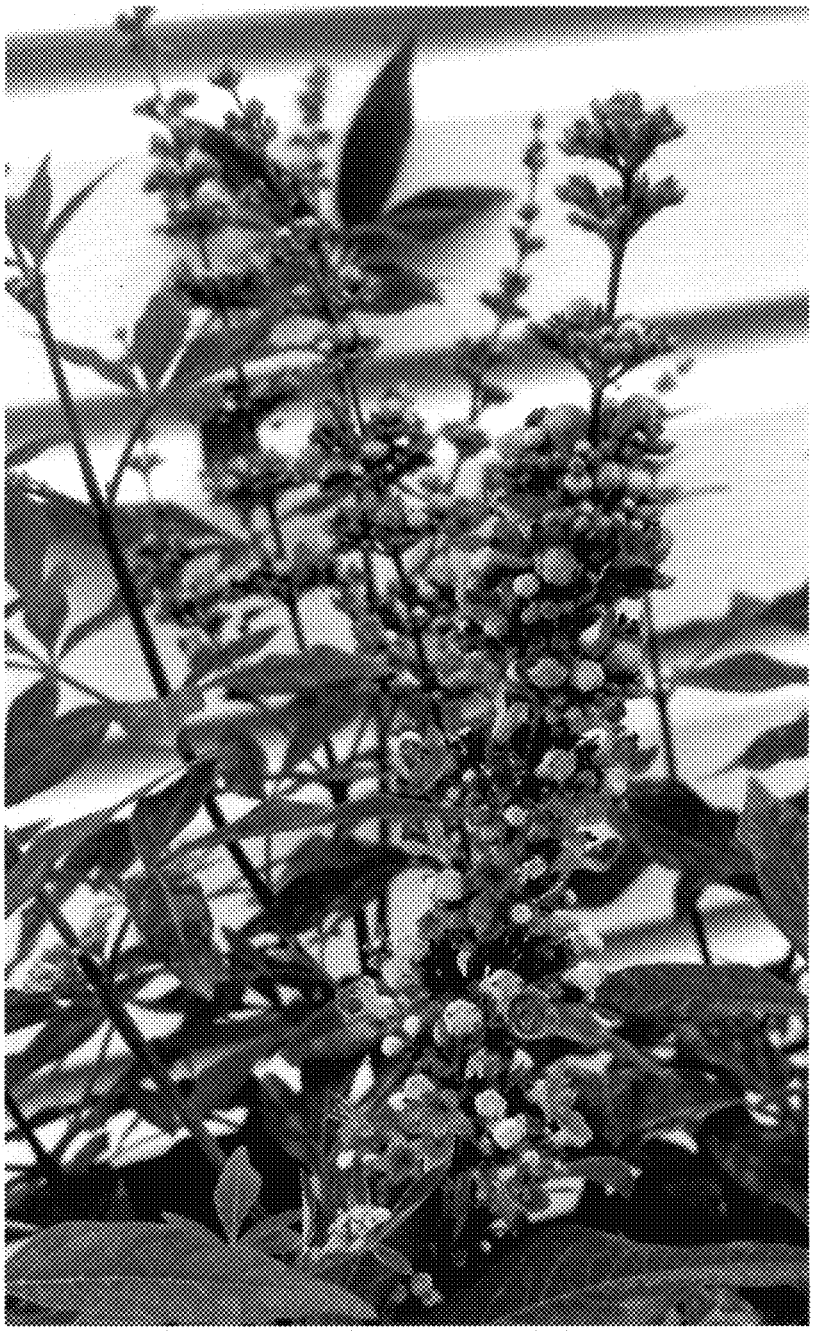

The photograph in FIG. 3 provides a close-up view of an inflorescence of 'Bailtexthree' in bloom.

Figure 4:
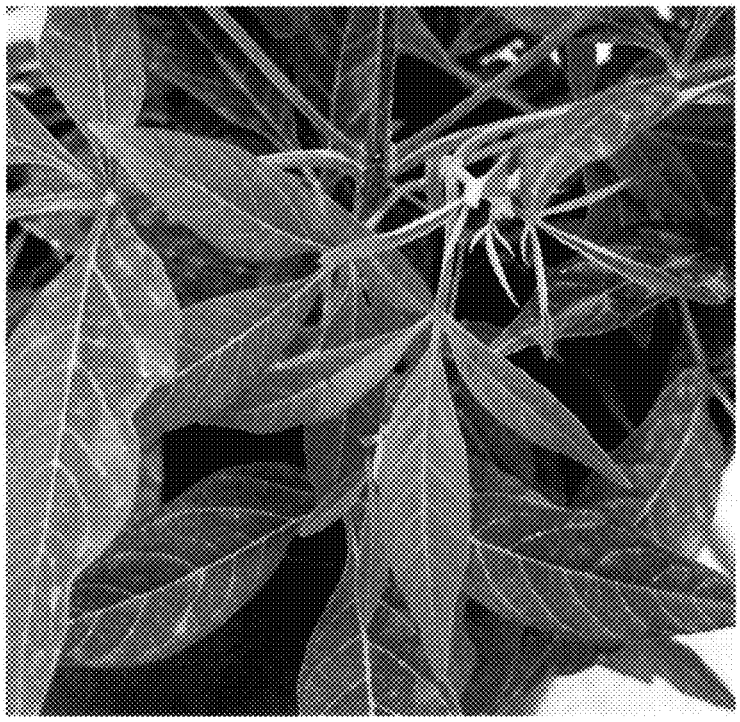

The photograph in FIG. 4 provides a close-up view of the foliage of 'Bailtexthree'.

Figure 5:
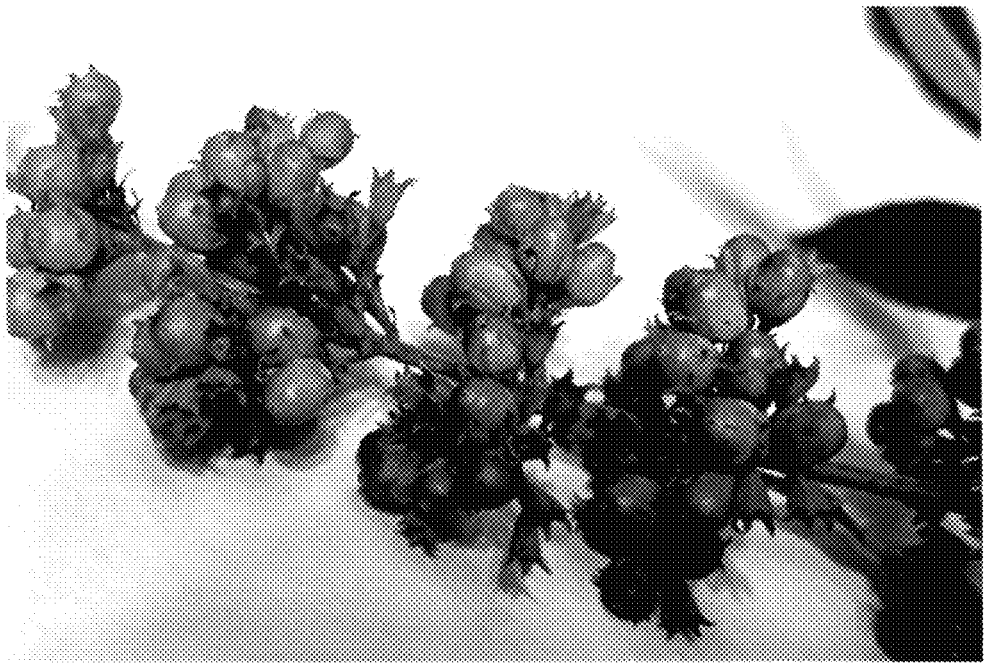

The photograph in FIG. 5 provides a close-up view of the fruit of 'Bailtexthree'.

The colors in the photographs are as close as possible with the digital photography and printing techniques utilized and the color codes in the detailed botanical description accurately describe the colors of the new *Vitex*.

DETAILED BOTANICAL DESCRIPTION

The following is a detailed description of plants 2 year in age as grown in 2-gallon containers in Cottage Grove, Minn.

The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period.*—Mid June to late summer in Georgia.

*Plant type.*—Deciduous flowering shrub.

*Plant habit.*—Compact and rounded to upright plant habit.

*Height and spread.*—An average of 47 cm in height and 56 cm in width as a 2-year-old plant in a container, reaches 1.8 m to 2.1 m in height and 2.4 m to 3 m in spread in the landscape.

*Hardiness.*—At least in U.S.D.A. Zones 6 to 9.

*Diseases and pests.*—Resistance to leaf spot (causative agent unknown) has been observed, no susceptibility or resistance to other diseases or pests has been observed.

*Root description.*—156A in color, young roots are fibrous, older roots become woody.

*Propagation.*—Softwood stem cuttings.

*Root development.*—An average of 6 weeks for root initiation and an average of 3 months to produce a young rooted plant.

*Growth rate.*—Moderately vigorous.

Branch description:

*Branch strength.*—Strong.

*Branch length.*—Main; 8 cm in length, 5 mm in diameter, lateral; 22 cm in length, 4 mm in diameter.

*Branch quantity.*—Main; 2, lateral; 2 to 4 per main branch.

*Branch aspect.*—Held in upright to outward angles.

*Branch shape.*—Young; flattened, mature; tetragonal.

*Branch color.*—Young and mature stems; N199A, old wood; 199D.

*Branch surface.*—Young and mature stems; tomentulose, old wood glabrous.

*Branching habit.*—Freely and multi-branching habit.

*Internode length.*—Ranging from 2 cm to 8 cm.

Foliage description:

*Leaf number.*—An average of 31 per lateral branch.

*Leaf arrangement.*—Opposite, palmate.

*Leaf shape.*—Whole leaf; ovate, leaflet; elliptic to lanceolate.

*Leaf size.*—Whole leaf; 11 cm in length, 15 cm in length, leaflet; 10 cm in length, 3 cm in width.

*Leaf division.*—Compound with 3 to 4 leaflets.

*Leaflet base.*—Cuneate.

*Leaflet apex.*—Acuminate.

*Leaflet margin.*—Entire.

*Leaflet venation.*—Pinnate, upper and lower surface color; 161A.

*Leaflet attachment.*—Petiolate.

*Leaflet surface.*—Both surfaces tomentulose and matte.

*Leaf color.*—Young upper surface; 144A, young lower surface; 148B, mature upper surface; NN137B, mature lower surface; 148B.

*Petioles.*—Average of 3.5 cm in length and 2 mm in diameter, both surfaces tomentulose, N199A.

*Petiolules.*—Average of 1 cm in length and 1.5 mm in width, both surfaces tomentulose, N199A and NN137B.

Flower description:

*Inflorescence type.*—Terminal racemose-panicle.

*Inflorescence size.*—An average of 28 cm in height and 26 cm in width.

*Lastingness of inflorescence.*—Inflorescences are showy for an average of 2 weeks, individual flowers last an average of 2 days, self-cleaning.

*Inflorescence quantity.*—3 per lateral branch, 21 per plant.

*Fragrance.*—Very faint, slightly musky.

*Quantity of flowers.*—An average of 330 flowers per inflorescence.

*Flower type.*—Bilabiate (one larger petal and one 4-lobed).

*Flower size.*—An average of 1.4 cm in width and 1 cm in depth.

*Flower buds.*—Obovate in shape, average of 5 mm in length, 4 mm in depth, surface is glabrous, color; young buds 97D, mature buds 91C.

*Flower aspect.*—Outward.

*Pedicel.*—Strong, an average of 3 mm in length and 1 mm in diameter, surface is tomentose, color; 144B, very slightly flushed with N186C.

*Peduncle.*—Strong, an average of 1.4 cm in length and 2 mm in diameter, surface is tomentose, color; N199A.

*Petals.*—5, petals are fused into base to form the corolla tube, tube is an average of 6 mm in length and 2 mm in width, both surfaces 76A in color, center lower petal; cupped downward, 7 mm in length, 6 mm in width, oblong shape, rounded apex, both surfaces glabrous and velvety, upper surface center edges moderately covered with tuffs of tomentose hairs, 0.4 mm in length, 92C and N92B in color, undulate margins, other petals; slightly cupped, 4 mm in length, 3 mm in width, pointed shape, acute apex, both surfaces glabrous and velvety, entire margins, color; when opening upper surface N82A and 83A, when opening lower surface 91C, when fully open upper surface 92A and 91B, margins 83A, center of lower center petal N92C, very slightly flushed with 71B, fully open lower surface 76C, margins 76A, when both surfaces fade and start to diminish N92B.

*Calyx.*—Consists of 5 fused sepals with acute apices, an average of 5 mm in length and 3 mm in diameter.

*Sepals.*—An average of 5 in a single whorl, fused at the base, elliptical in shape, entire margins, acute apex, both surfaces are tomentose, an average of 1 mm in length and 0.8 mm in width, color; outer surface 140D, flushed with N77A at the tips, inner surface 140A, flushed with N77A at the tips.

Reproductive organs:

*Gynoecium.*—Pistil; 1, an average of 3 mm in length, 0.4 mm in width, glabrous surface, style; an average of 3 mm in length and 84A in color, stigma; forked, 0.7 mm in length and 155C in color, ovary; inferior, 155C in color and 1 mm in diameter.

*Androecium.*—Stamens; 4 per flower attached to the inner base of the corolla tube, 5 mm in length, glabrous surface, anther; dorsifixed, 1 mm in length, 0.5 mm in width, 203C in color, filaments; 5 mm in length, 91C in color, pollen; is moderate in quantity and 11C in color.

*Fruit and seed.*—Average of 90 per branch, drupe, round in shape, surface is glossy and glabrous, average of 4 mm length and diameter, immature color; 145A, mature color; a blend of 145A and 183A, each drupe contains one seed that is about 3 mm in length and diameter, dull surface, 145C in color.

It is claimed:

1. A new and distinct cultivar of *Vitex* plant named 'Bailtexthree' as herein illustrated and described.

* * * * *